(12) United States Patent
Kitamura

(10) Patent No.: US 10,217,942 B2
(45) Date of Patent: Feb. 26, 2019

(54) ORGANIC SEMICONDUCTOR ELEMENT, MANUFACTURING METHOD THEREOF, COMPOUND, COMPOSITION FOR FORMING ORGANIC SEMICONDUCTOR FILM, AND ORGANIC SEMICONDUCTOR FILM

(71) Applicant: FUJIFILM CORPORATION, Minato-ku, Tokyo (JP)

(72) Inventor: Tetsu Kitamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 6 days.

(21) Appl. No.: 15/497,223

(22) Filed: Apr. 26, 2017

(65) Prior Publication Data

US 2017/0229655 A1 Aug. 10, 2017

Related U.S. Application Data

(63) Continuation of application No. PCT/JP2015/081179, filed on Nov. 5, 2015.

(30) Foreign Application Priority Data

Nov. 14, 2014 (JP) .................................. 2014-231214

(51) Int. Cl.
*H01L 51/00* (2006.01)
*C08G 61/12* (2006.01)
*H01L 29/786* (2006.01)
*H01L 51/05* (2006.01)

(52) U.S. Cl.
CPC .......... *H01L 51/0036* (2013.01); *C08G 61/12* (2013.01); *C08G 61/123* (2013.01); *C08G 61/125* (2013.01); *C08G 61/126* (2013.01); *H01L 29/786* (2013.01); *H01L 51/0035* (2013.01); *H01L 51/0043* (2013.01); *H01L 51/05* (2013.01); *C08G 2261/124* (2013.01); *C08G 2261/141* (2013.01); *C08G 2261/146* (2013.01); *C08G 2261/148* (2013.01); *C08G 2261/1412* (2013.01); *C08G 2261/1426* (2013.01); *C08G 2261/1428* (2013.01); *C08G 2261/1452* (2013.01); *C08G 2261/18* (2013.01); *C08G 2261/228* (2013.01); *C08G 2261/312* (2013.01); *C08G 2261/314* (2013.01); *C08G 2261/3221* (2013.01); *C08G 2261/3223* (2013.01); *C08G 2261/3225* (2013.01); *C08G 2261/3241* (2013.01); *C08G 2261/3242* (2013.01); *C08G 2261/3243* (2013.01); *C08G 2261/3244* (2013.01); *C08G 2261/334* (2013.01); *C08G 2261/344* (2013.01); *C08G 2261/414* (2013.01); *C08G 2261/92* (2013.01); *C08L 2205/02* (2013.01); *H01L 51/0003* (2013.01); *H01L 51/0541* (2013.01); *H01L 51/0545* (2013.01); *H01L 51/0558* (2013.01)

(58) Field of Classification Search
None
See application file for complete search history.

(56) References Cited

U.S. PATENT DOCUMENTS

2014/0353628 A1    12/2014  Facchetti

FOREIGN PATENT DOCUMENTS

| JP | 2007-516315 A | 6/2007 |
| JP | 2014-514413 A | 6/2014 |
| WO | 2007/003520 A1 | 1/2007 |

OTHER PUBLICATIONS

Extended European Search Report dated Oct. 13, 2017, issued in corresponding EP Patent Application No. 15859941.5.
Kai Zhang and Bernd Tieke: "Highly Luminescent Polymers Containing the 2, 3, 5, 6-Tetraarylated Pyrrolo [3, 4-c] pyrrole-1, 4-dione (N-Aryl DPP) Chromophore in the Main Chain", Macromolecules, American Chemical Society, US, vol. 41, No. 20, Oct. 28, 2008, pp. 7287-7295, XP002545096, ISSN: 0024-9297, DOI: 10. 1021/MA801376R.

*Primary Examiner* — Tanisha Diggs
(74) *Attorney, Agent, or Firm* — SOLARIS Intellectual Property Group, PLLC

(57) ABSTRACT

An object of the invention is to provide an organic semiconductor element having high mobility and excellent temporal stability under high humidity, and a manufacturing method thereof. Another object is to provide a novel compound suitable for an organic semiconductor. Still another object is to provide an organic semiconductor film having high mobility and excellent temporal stability under high humidity and a composition for forming an organic semiconductor film that can suitably form the organic semiconductor film.
The organic semiconductor element according to the invention includes an organic semiconductor layer containing an organic semiconductor having a repeating unit represented by Formula 1.

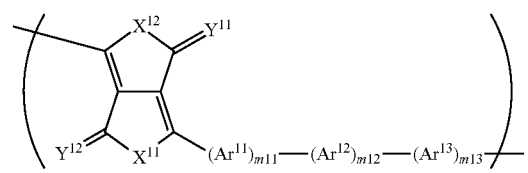

(1)

20 Claims, 1 Drawing Sheet

ORGANIC SEMICONDUCTOR ELEMENT, MANUFACTURING METHOD THEREOF, COMPOUND, COMPOSITION FOR FORMING ORGANIC SEMICONDUCTOR FILM, AND ORGANIC SEMICONDUCTOR FILM

CROSS-REFERENCE TO RELATED APPLICATION

This application is a continuation application of International Application No. PCT/JP2015/081179, filed Nov. 5, 2015, the disclosure of which is incorporated herein by reference in its entirety. Further, this application claims priority from Japanese Patent Application No. 2014-231214, filed Nov. 14, 2014, the disclosure of which is incorporated herein by reference in its entirety.

BACKGROUND OF THE INVENTION

1. Field of the Invention

The invention relates to an organic semiconductor element, a manufacturing method thereof, a compound, a composition for forming an organic semiconductor film, and an organic semiconductor film.

2. Description of the Related Art

An organic transistor having an organic semiconductor film (organic semiconductor layer) is used in a field effect transistor (FET) used in a liquid crystal display or an organic EL display, RFID (RF tag), and the like, because lightening of weight, cost reduction and flexibilization can be achieved.

As the organic semiconductor in the related art, those disclosed in JP2007-516315A and JP2014-514413A are known.

SUMMARY OF THE INVENTION

An object to be achieved by the present invention is to provide an organic semiconductor element having high mobility and excellent temporal stability under high humidity, and a manufacturing method thereof.

Another object to be achieved by the present invention is to provide a novel compound which is suitable as an organic semiconductor.

Still another object to be achieved by the present invention is to provide an organic semiconductor film having high mobility and excellent temporal stability under high humidity and a composition for forming an organic semiconductor film that can suitably form the organic semiconductor film.

The objects of the invention were solved by the means described in <1>, <5>, <10>, <15>, or <16> below. <2> to <4>, <6> to <9>, <11> to <14>, and <17> to <20> which are preferable embodiments are also described below.

<1> An organic semiconductor element comprising:

an organic semiconductor layer containing an organic semiconductor having a repeating unit represented by Formula 1,

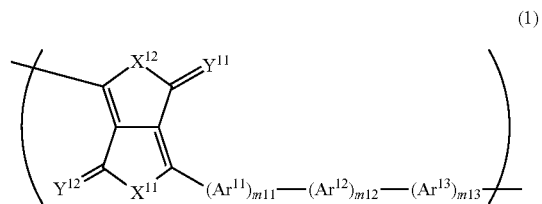

(1)

in Formula 1, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, and m13 represents an integer of 0 to 2.

<2> The organic semiconductor element according to <1>, in which both of $X^{11}$ and $X^{12}$ are O or S.

<3> The organic semiconductor element according to <1> or <2>, in which both of $Y^{11}$ and $Y^{12}$ are O or S.

<4> The organic semiconductor element according to any one of <1> to <3>, in which the repeating unit represented by Formula 1 is a repeating unit represented by Formula 2,

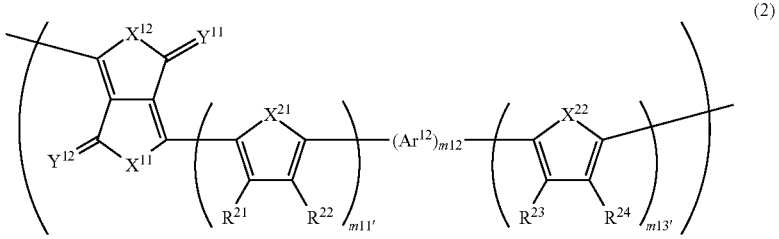

(2)

in Formula 2, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}{}_2$, O, S, Se, and $SiR^{11'}{}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, and m13' represents an integer of 0 to 2.

<5> A compound comprising: a repeating unit represented by Formula 1,

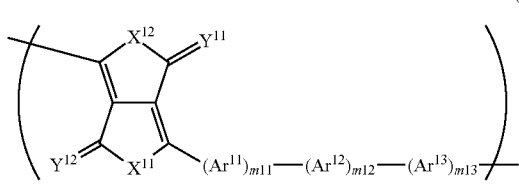
(1)

in Formula 1, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, and m13 represents an integer of 0 to 2.

<6> The compound according to <5>, in which both of $X^{11}$ and $X^{12}$ are O or S.

<7> The compound according to <5> or <6>, in which both of $Y^{11}$ and $Y^{12}$ are O or S.

<8> The compound according to any one of <5> to <7>, in which the repeating unit represented by Formula 1 is a repeating unit represented by Formula 2,

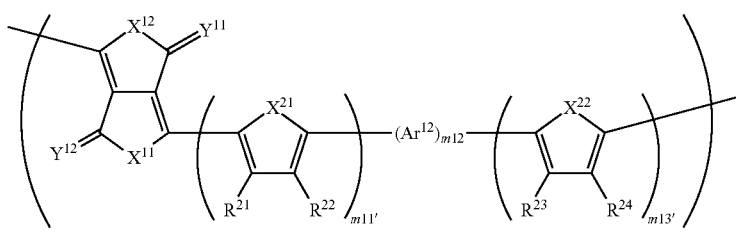
(2)

in Formula 2, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}{}_2$, O, S, Se, and $SiR^{11'}{}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, and m13' represents an integer of 0 to 2.

<9> The compound according to any one of <5> to <8>, which is an organic semiconductor.

<10> A composition for forming an organic semiconductor film, comprising: a compound having a repeating unit represented by Formula 1; and a solvent,

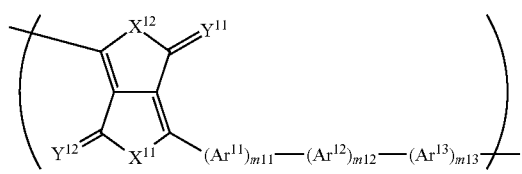
(1)

in Formula 1, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, and m13 represents an integer of 0 to 2.

<11> The composition for forming an organic semiconductor film according to <10>, in which both of $X^{11}$ and $X^{12}$ are O or S.

<12> The composition for forming an organic semiconductor film according to <10> or <11>, in which both of $Y^{11}$ and $Y^{12}$ are O or S.

<13> The composition for forming an organic semiconductor film according to any one of <10> to <12>, in which the repeating unit represented by Formula 1 is a repeating unit represented by Formula 2,

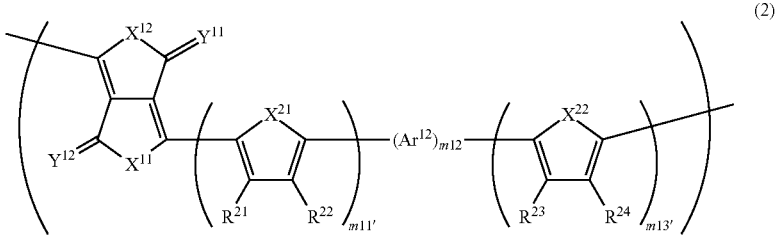

in Formula 2, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}{}_2$, O, S, Se, and $SiR^{11'}{}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, and m13' represents an integer of 0 to 2.

<14> The composition for forming an organic semiconductor film according to any one of <10> to <13>, further comprising: a binder polymer.

<15> A method of manufacturing an organic semiconductor element, comprising: a coating step of coating a substrate with the composition for forming an organic semiconductor film according to any one of <10> to <14>.

<16> An organic semiconductor film comprising: a compound having a repeating unit represented by Formula 1,

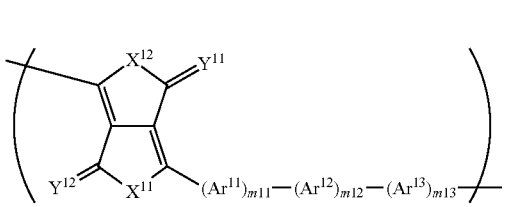

in Formula 1, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, and m13 represents an integer of 0 to 2.

<17> The organic semiconductor film according to <16>, in which both of $X^{11}$ and $X^{12}$ are O or S.

<18> The organic semiconductor film according to <16> or <17>, in which both of $Y^{11}$ and $Y^{12}$ are O or S.

<19> The organic semiconductor film according to any one of <16> to <18>, in which the repeating unit represented by Formula 1 is a repeating unit represented by Formula 2,

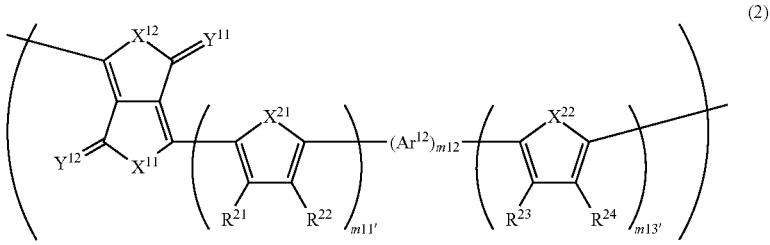

in Formula 2, $X^{11}$ and $X^{12}$ each independently represent any one of $CH_2$, $CR^{11}{}_2$, O, S, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}{}_2$, O, S, Se, or $SiR^{11'}{}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, and m13' represents an integer of 0 to 2.

<20> The organic semiconductor film according to any one of <16> to <19>, which is manufactured by a solution coating method.

According to the present invention, it is possible to provide an organic semiconductor element having high mobility and excellent temporal stability under high humidity and a manufacturing method thereof.

According to the present invention, it is possible to provide a novel compound suitable for an organic semiconductor.

According to the present invention, it is possible to provide an organic semiconductor film having high mobility and excellent temporal stability under high humidity and a composition for forming an organic semiconductor film that can suitably form the organic semiconductor film.

DESCRIPTION OF THE PREFERRED EMBODIMENTS

Figure 1:
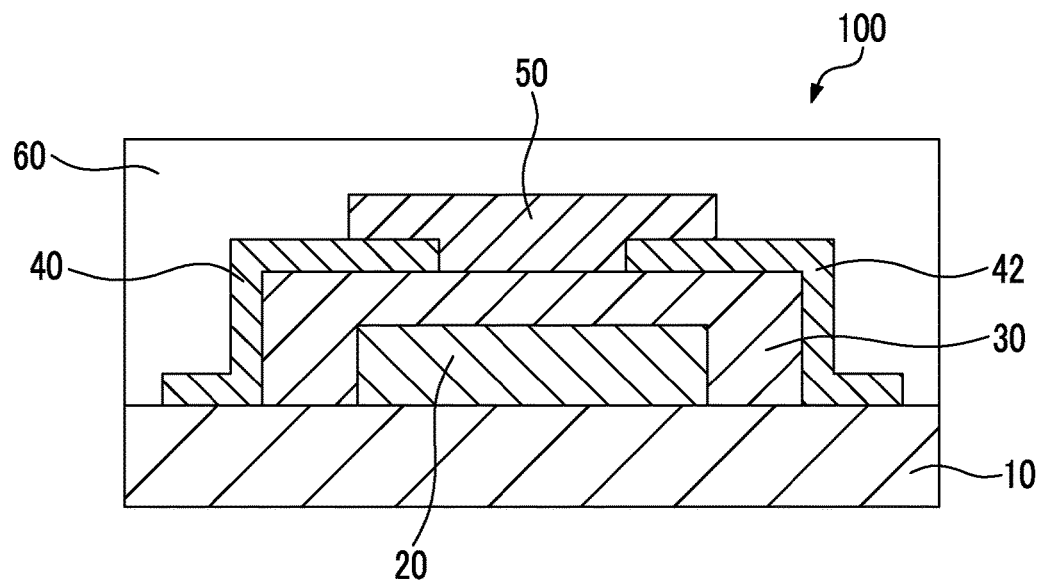
FIG. 1 is a schematic cross-sectional view of an aspect of an organic semiconductor element of the present invention.

Hereinafter, the contents of the present invention will be specifically described. The constituents in the following description will be explained based on typical embodiments of the present invention, but the present invention is not limited to the embodiments. In the specification of the present application, "to" is used to mean that the numerical values listed before and after "to" are a lower limit and an upper limit respectively. Furthermore, in the present invention, an organic EL element refers to an organic electroluminescence element.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, in some cases, a chemical structural formula is described as a simplified structural formula in which a hydrogen atom is omitted.

In the present invention, "mass %" and "weight %" have the same definition, and "part by mass" and "part by weight" have the same definition.

In the present invention, a combination of two or more preferred aspects is more preferable.

(Organic Semiconductor Element)

The organic semiconductor element according to the present invention has an organic semiconductor layer containing an organic semiconductor (hereinafter, also referred to as a "specific organic semiconductor compound") that has a repeating unit represented by Formula 1.

As a result of diligent research, the present inventors found that, if the specific organic semiconductor compound was contained, the obtained organic semiconductor element or the obtained organic semiconductor film had high mobility and excellent temporal stability under high humidity, so as to complete the present invention.

The detailed mechanism of exhibiting the effects is not clear, but it is considered that the specific organic semiconductor compound causes the film quality to be even, and thus temporal stability under high humidity becomes excellent.

<Specific Organic Semiconductor Compound>

In the present invention, the specific organic semiconductor compound has a repeating unit represented by Formula 1 below.

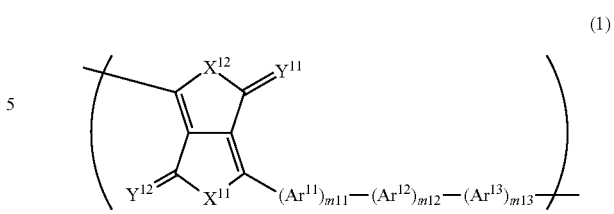

In Formula 1, $X^{11}$ and $X^{12}$ each independently represent any one of $CH_2$, $CR^{11}_2$, O, S, Se, and $SiR^{11}_2$, $R^{11}$'s each independently represent a monovalent organic group, $Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$, $R^{12}$'s each independently represent a monovalent organic group, a plurality of $R^{13}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, and m13 represents an integer of 0 to 2.

The specific organic semiconductor compound according to the present invention is a novel compound.

The specific organic semiconductor compound according to the present invention can be suitably used in an organic semiconductor element, an organic semiconductor film, and a composition for forming an organic semiconductor film.

In Formula 1, $X^{11}$ and $X^{12}$ each independently represent any one of $CH_2$, $CR^{11}_2$, O, S, Se, and $SiR^{11}_2$. It is preferable that $X^{11}$ and $X^{12}$ each independently represent O or S, both of $X^{11}$ and $X^{12}$ are O or S, and it is more preferable that both of $X^{11}$ and $X^{12}$ are S.

$X^{11}$ and $X^{12}$ may be different from each other. In view of manufacturing suitability, it is preferable that $X^{11}$ and $X^{12}$ are the same with each other.

$R^{11}$'s each independently and preferably represent a monovalent organic group, an alkyl group, or an aryl group, more preferably an alkyl group having 1 to 20 carbon atoms and an aryl group having 6 to 20 carbon atoms, and even more preferably an alkyl group having 6 to 20 carbon atoms or a phenyl group. The alkyl group may have any one of a linear shape, a branched shape, and a cyclic shape.

$Y^{11}$ and $Y^{12}$ each independently represent O, S, N—CN, or $CQ_2$, Q represents CN, $CF_3$, C(=O)$R^{12}$, C(=O)O$R^{12}$, or $SO_2R^{12}$. It is preferable that $Y^{11}$ and $Y^{12}$ each independently represent O or S, it is more preferable that both of $Y^{11}$ and $Y^{12}$ are O or S, and it is even more preferable that both of $Y^{11}$ and $Y^{12}$ are S.

$R^{12}$'s each independently and preferably represent a monovalent organic group, an alkyl group, or an aryl group, more preferably an alkyl group having 1 to 20 carbon atoms and an aryl group having 6 to 20 carbon atoms, even more preferably an alkyl group having 1 to 20 carbon atoms, and particularly preferably an alkyl group having 6 to 20 carbon atoms. The alkyl group may be any one of a linear shape, a branched shape, and a cyclic shape.

A plurality of $R^{12}$'s may be bonded to each other to form a ring. The ring formed with the plurality of $R^{12}$ may be further fused with an aromatic ring such as a benzene ring.

$Ar^{11}$, $Ar^{12}$, and $Ar^{13}$ each independently represent an aromatic hydrocarbon group, an aromatic heterocyclic group, a vinylene group, or an ethynylene group.

$Ar^{11}$ and $Ar^{13}$ are preferably an aromatic hydrocarbon group or an aromatic heterocyclic group. $Ar^{11}$ and $Ar^{13}$ may have a polycyclic structure but are preferably a monocyclic structure.

The aromatic hydrocarbon group is preferably an arylene group having 6 to 20 carbon atoms and more preferably a phenylene group or a naphthylene group.

The heteroatoms of the aromatic hetero ring are not particularly limited. However, examples thereof include S, O, N, and Se. Examples of the aromatic heterocyclic group include groups obtained by removing two hydrogen atoms from a ring selected from the group consisting of a thiophene ring, a furan ring, a pyran ring, a pyrrole ring, a pyridine ring, a pyrazine ring, a pyrimidine ring, a pyridazine ring, a selenophene ring, an imidazole ring, and a thienothiophene ring. A group obtained by removing two hydrogen atoms from a ring selected from the group consisting of a thiophene ring, a furan ring, a pyrrole ring, a pyridine ring, a selenophene ring, and a thienothiophene ring is preferable, and a group obtained by removing two hydrogen atoms from a thiophene ring is more preferable.

An aromatic hydrocarbon group or an aromatic heterocyclic group may have a substituent. Examples of the preferable substituent include an alkyl group. An alkyl group having 1 to 20 carbon atoms is preferable, and an alkyl group having 8 to 20 carbon atoms is more preferable.

In view of manufacturing suitability, it is preferable that $Ar^{11}$ and $Ar^{13}$ may be the same with each other.

$Ar^{12}$ represent an aromatic hydrocarbon group, an aromatic heterocyclic group, a vinylene group, or an ethynylene group. A fused polycyclic aromatic group, a vinylene group, or a thienylene group is preferable.

The aromatic hydrocarbon group is preferably an arylene group having 6 to 20 carbon atoms and more preferably a group obtained by removing one hydrogen atom from a ring selected from the group consisting of a benzene ring, a naphthalene ring, an anthracene ring, and a pyrene ring.

The heteroatom of the aromatic hetero ring is not particularly limited, and examples thereof include S, O, N, Se, and Si. Examples of the aromatic heterocyclic group include a group obtained by removing two hydrogen atoms from a ring selected from the group consisting of a thiophene ring, a furan ring, a pyran ring, a pyrrole ring, a pyridine ring, a pyrazine ring, a pyrimidine ring, a pyridazine ring, a selenophene ring, an imidazole ring, and a thienothiophene ring. The aromatic heterocyclic group is preferably a group obtained by removing two hydrogen atoms from a ring selected from the group consisting of a thiophene ring, a furan ring, a pyrrole ring, a pyridine ring, a selenophene ring, and a thienothiophene ring, more preferably a group obtained by removing two hydrogen atoms from a ring selected from the group consisting of a thiophene ring and a thienothiophene ring, and even more preferably a group obtained by removing two hydrogen atoms from a thiophene ring.

The aromatic hydrocarbon group or the aromatic heterocyclic group each may have a substituent. Examples of the preferable substituent include an alkyl group, and the preferable substituent is preferably an alkyl group having 1 to 20 carbon atoms and more preferably an alkyl group of 8 to 20 carbon atoms.

$Ar^{12}$ preferably represents a fused polycyclic aromatic group in which a plurality of aromatic hydrocarbon groups or a plurality of aromatic heterocyclic groups are fused. In a case where $Ar^{12}$ represents a fused polycyclic aromatic group, a fused ring having three to seven rings is preferable, and a fused ring having three to five rings is more preferable. In the fused ring, a non-aromatic heterocyclic group such as cyclotetramethylene silane may be included.

In a case where $Ar^{12}$ represents a fused polycyclic aromatic group, a structure represented by any one of Formula AR-1 to AR-10 below is preferable.

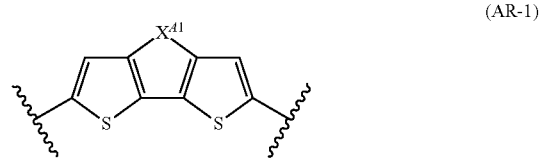

(AR-1)

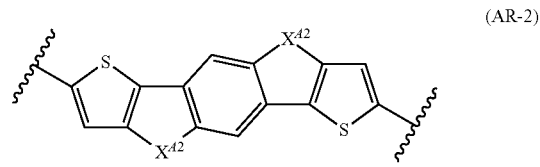

(AR-2)

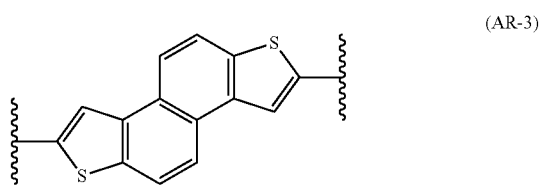

(AR-3)

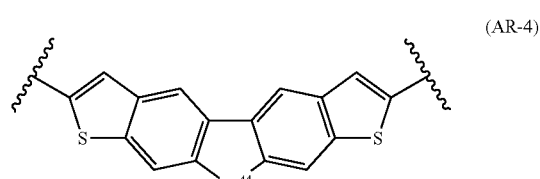

(AR-4)

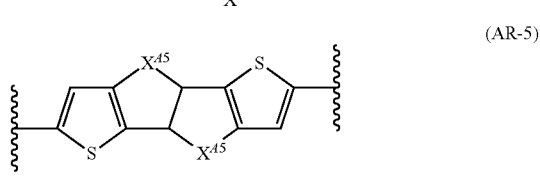

(AR-5)

(AR-6)

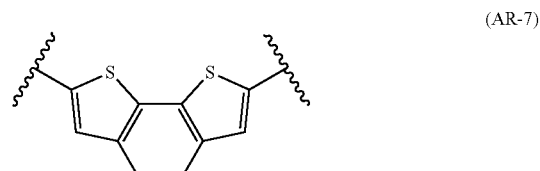

(AR-7)

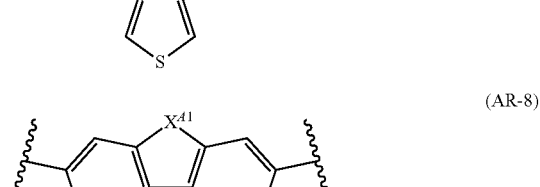

(AR-8)

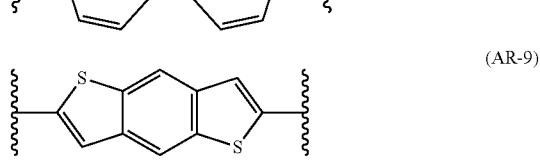

(AR-9)

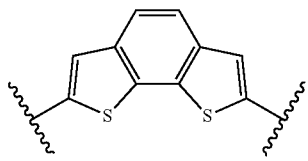
(AR-10)

In Formulae AR-1 to AR-10, $X^{A1}$, $X^{A2}$, $X^{A4}$, and $X^{A5}$ each independently represent any one of S, O, $CR^{AR}_2$, $NR^{AR}$, and $SiR^{AR}_2$, and $R^{AR}$'s each independently represent a monovalent organic group. $R^{AR}$ is preferably an alkyl group having 8 to 20 carbon atoms.

Among these, AR-1 to AR-6, AR-9, or AR-10 is preferable, any one of AR-1 to AR-5 is more preferable, and AR-1 or AR-5 is even more preferable.

The polycyclic aromatic hydrocarbon group or the polycyclic aromatic heterocyclic group may have a substituent. Examples of the preferable substituent include an alkyl group, an alkyl group having 1 to 30 carbon atoms is preferable and an alkyl group having 8 to 20 carbon atoms is more preferable.

m11 preferably represents an integer of 0 to 2, m12 represents an integer of 0 to 4, m13 represents an integer of 0 to 2, and a sum of m11, m12, and m13 is preferably 1 or greater.

In a case where $Ar^{12}$ is a vinylene group or an ethynylene group, m12 preferably represent 1, and m11 and m13 each independently and preferably represent 1 or 2.

In a case where $Ar^{12}$ is an aromatic hydrocarbon group or an aromatic heterocyclic group, m12 is preferably 1 or 2, m11 and m13 each independently represent and preferably 0 or 1.

In a case where $Ar^{12}$ is a fused polycyclic aromatic group, m12 is preferably 1, m11 and m13 each independently and preferably represent 0 or 1.

The repeating unit represented by Formula 1 is preferably a repeating unit represented by Formula 2.

and an alkyl group having 1 to 15 carbon atoms is even more preferable. The alkyl group may be any one of a linear shape, a branched shape, and a cyclic shape.

$R^{21}$ to $R^{24}$ each independently represent a hydrogen atom or a monovalent organic group, an alkyl group having 1 to 20 carbon atoms is preferable, and an alkyl group having 8 to 20 carbon atoms is more preferable.

m11' represents an integer of 0 to 2, m13' represents an integer of 0 to 2, and a sum of m11', m12, and m13' is preferably 1 or greater.

In a case where $Ar^{12}$ is a vinylene group or an ethynylene group, m12 represents 1, m11' and m13' each independently represent and preferably 1 or 2.

In a case where $Ar^{12}$ is an aromatic hydrocarbon group or an aromatic heterocyclic group, m12 is preferably 1 or 2, m11' and m13' each independently represent and preferably 0 or 1.

In a case where $Ar^{12}$ is a fused polycyclic aromatic group, m12 is preferably 1, m11' and m13' each independently and preferably represent 0 or 1.

In the specific organic semiconductor compound, the content of the repeating unit represented by Formula 1 is preferably 60 to 100 mass %, more preferably 80 to 100 mass %, and even more preferably 90 to 100 mass % with respect to a total mass of the specific organic semiconductor compound.

The weight-average molecular weight of the specific organic semiconductor compound is not particularly limited, but the weight-average molecular weight is preferably 1,000 to 2,000,000, more preferably 10,000 to 1,000,000, and even more preferably 50,000 to 500,000.

If the molecular weight is in the range described above, it is possible to cause solubility to the solvent and the film quality stability to be compatible with each other.

According to the present invention, a weight-average molecular weight and a number-average molecular weight are measured by a gel permeation chromatography method (GPC method) and can be obtained in terms of standard polystyrene. Specifically, for example, HLC-8220GPC

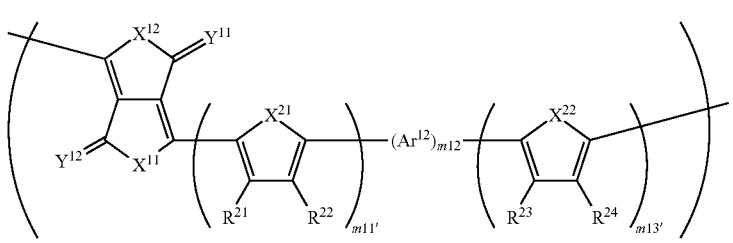

(2)

In Formula 2, $X^{11}$, $X^{12}$, $Y^{11}$, $Y^{12}$, $Ar^{12}$, and m12 are respectively the same as $X^{11}$, $X^{12}$, $Y^{11}$, $Y^{12}$, $Ar^{12}$, and m12 in Formula 1, the preferably ranges thereof are also the same, $X^{21}$ and $X^{22}$ each independently represent any one of $CH_2$, $CR^{11}_2$, O, S, Se, and $SiR^{11}_2$, $R^{11}$'s each independently represent a monovalent organic group, $R^{21}$ to $R^{24}$ each independently represent a hydrogen atom or a monovalent organic group, m11' represents an integer of 0 to 2, and m13' represents an integer of 0 to 2.

$X^{21}$ and $X^{22}$ each independently represent any one of O, S, Se, $NR^{12'}$, and $SiR^{12'}_2$, any one of O, S, and $NR^{12'}$ are more preferable, and S is even more preferable.

$R^{12'}$'s each independently represent a hydrogen atom or a monovalent organic group, an alkyl group is preferable, an alkyl group having 1 to 30 carbon atoms is more preferable, (manufactured by Tosoh Corporation) is used as GPC, three of TSKgeL SuperHZM-H, TSKgeL SuperHZ4000, TSKgeL SuperHZ2000 (manufactured by Tosoh Corporation, 4.6 mmID×15 cm) are used as columns, and THF (tetrahydrofuran) is used as an eluent. As the condition, the sample concentration is set as 0.35 mass %, a flow rate is set as 0.35 ml/min, a sample injection volume is set as 10 µl, a measurement temperature is set as 40° C., and an IR detector was used. A calibration curve is manufactured from eight samples of "standard sample TSK standard, polystyrene": "F-40", "F-20", "F-4", "F-1", "A-5000", "A-2500", "A-1000", and "n-propylbenzene" manufactured by Tosoh Corporation.

In an organic semiconductor layer described below, and an organic semiconductor film or a composition for forming an organic semiconductor film described below, only one specific organic semiconductor compound may be included, and two or more types of the specific organic semiconductor compounds may be included. However, in view of alignment, only one type is preferable.

Specific examples of the specific organic semiconductor compound represented by Formula 1 used in the present invention preferably include compounds (E-1 to E-22 and E-25) containing repeating units below, but the present invention is not limited thereto.

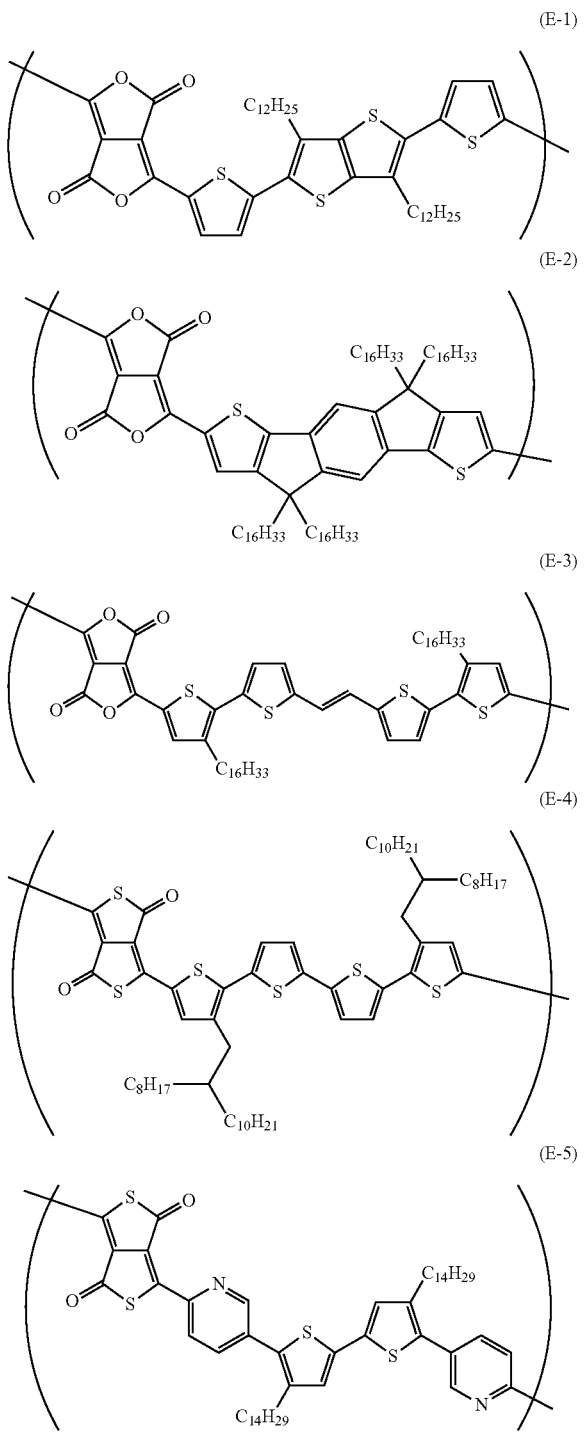

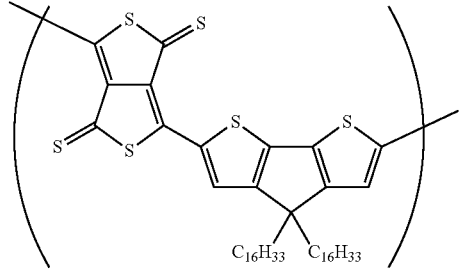

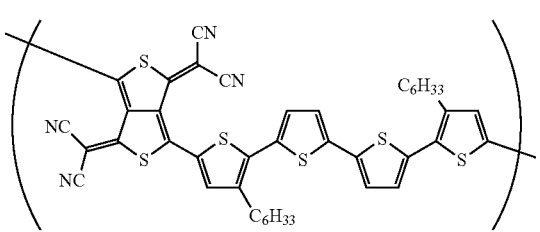

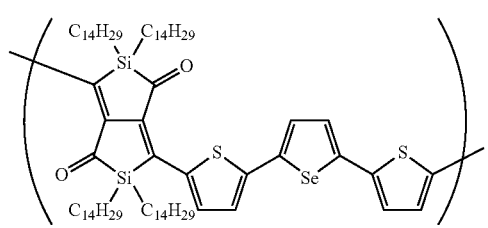

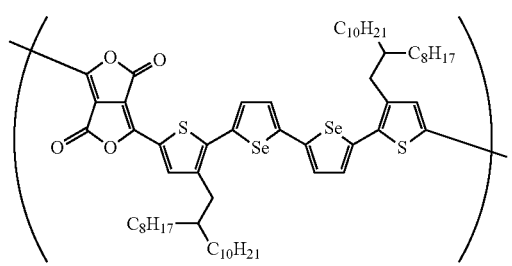

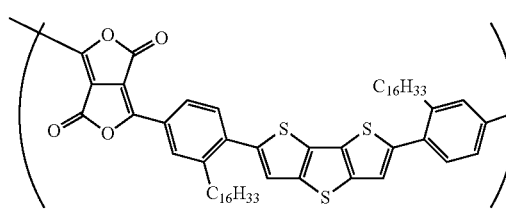

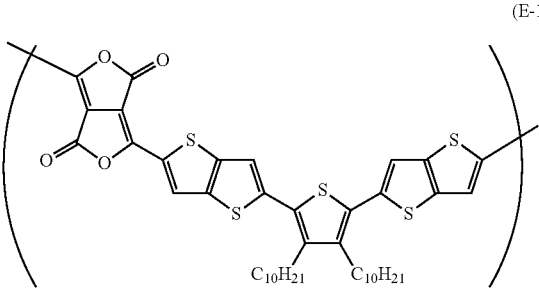

-continued
(E-12)
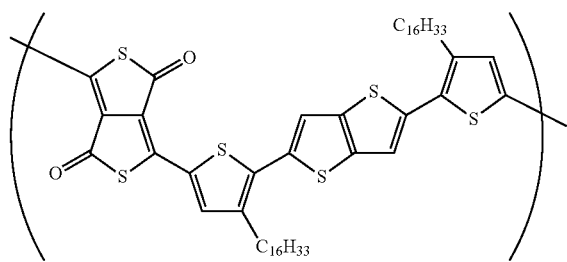
(E-13)
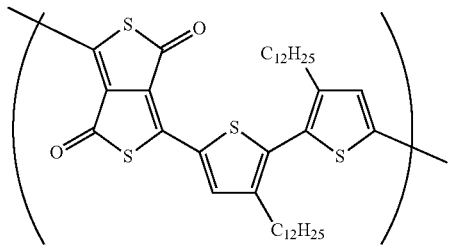
(E-14)
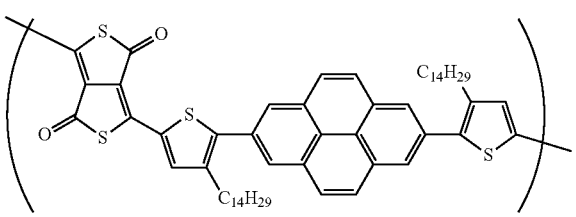
(E-15)
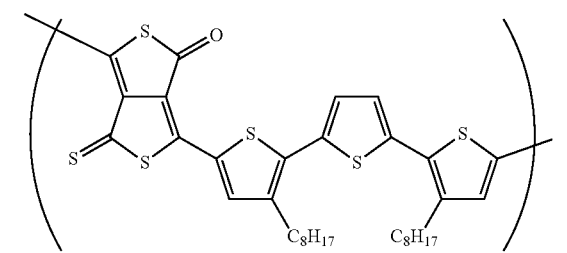
(E-16)
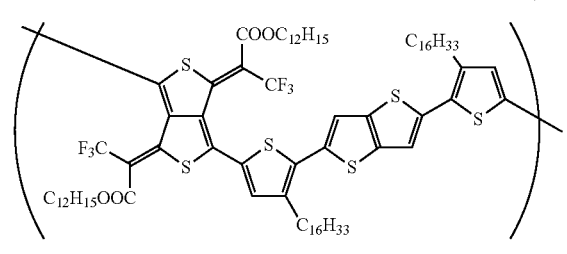
(E-17)
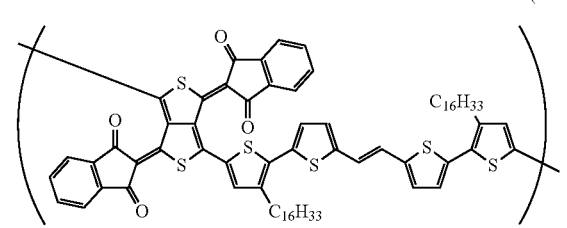
(E-18)
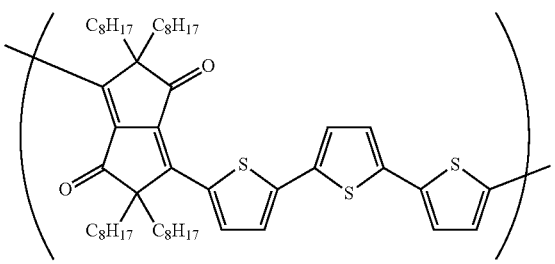
(E-19)
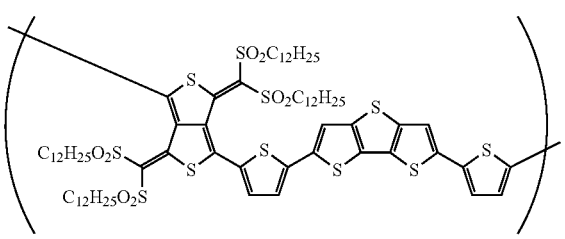
(E-20)
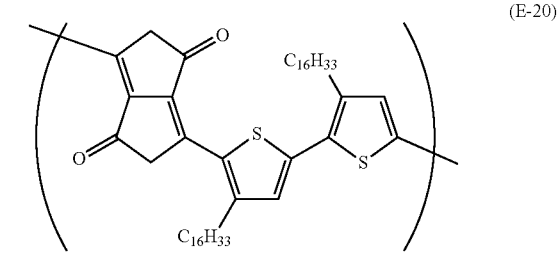
(E-21)
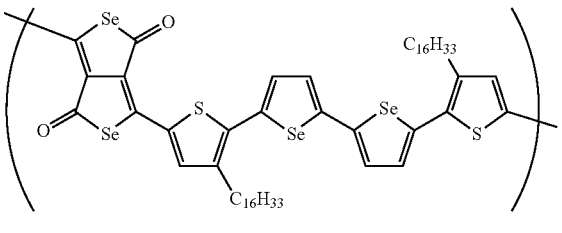
(E-22)
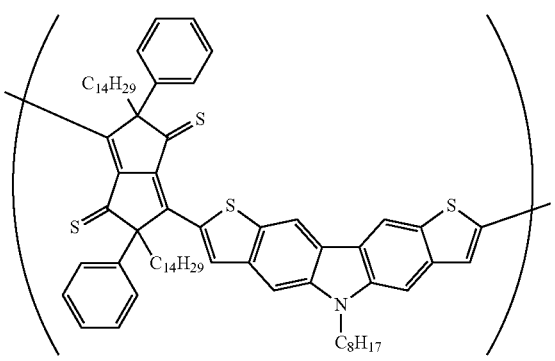

-continued

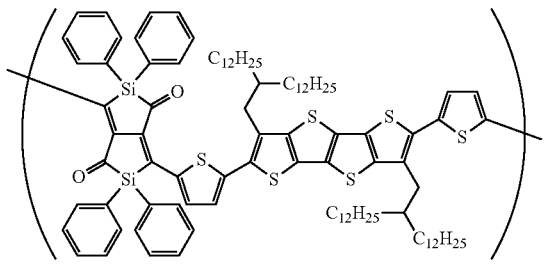

(E-25)

Among these, E-1 to E-4, E-6, E-9, E-12, E-13, and E-15 are preferable, and E-4, E-6, E-12, E-13, and E-15 are more preferable.

The synthesis method of the specific organic semiconductor compound is not particularly limited, and the specific organic semiconductor compound can be synthesized in the well-known methods. For example, the synthesis can be performed with reference to JP2011-168747A, Macromol., 2013, 46, 3887., and J. Org. Chem. 1985, 50, 1681.

In the organic semiconductor layer of the organic semiconductor element according to the present invention and the organic semiconductor film according to the present invention described below, the content of the specific organic semiconductor compound is preferably 30 to 100 mass %, more preferably 50 to 100 mass %, and even more preferably 70 to 100 mass % with respect to a total mass of the organic semiconductor layer or the organic semiconductor film. In a case where a binder polymer described below is not contained, the content is preferably 90 to 100 mass % and more preferably 95 to 100 mass % with respect to a total mass of the organic semiconductor layer or the organic semiconductor film.

(Compound)

The compound according to the present invention has a repeating unit represented by Formula 1.

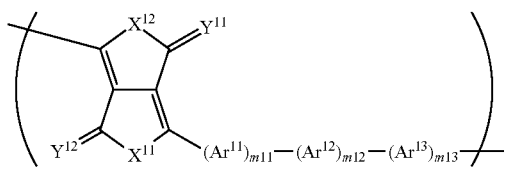

(1)

In Formula 1, $X^{11}$ and $X^{12}$ each independently represent any one of $CH_2$, $CR^{11}_2$, O, S, Se, and $SiR^{11}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, and m13 represents an integer of 0 to 2.

In Formula 1, $X^{11}$, $X^{12}$, $Y^{11}$, $Y^{12}$, $Ar^{11}$, $Ar^{12}$, $Ar^{13}$, m11, m12, and m13 respectively have the same meaning as $X^{11}$, $X^{12}$, $Y^{11}$, $Y^{12}$, $Ar^{11}$, $Ar^{12}$, $Ar^{13}$, m11, m12, and m13 in the specific organic semiconductor compound, and preferable aspects thereof are also the same.

The compound according to the present invention is preferably an organic semiconductor compound.

The content, the weight-average molecular weight, the specific examples, and the synthesis methods of the repeating unit represented by Formula 1 in compound according to the present invention are the same as those in the specific organic semiconductor compound, and preferably aspects thereof are also the same.

<Binder Polymer>

The organic semiconductor layer of the organic semiconductor element according to the present invention preferably contains the binder polymer.

The organic semiconductor element according to the present invention may be an organic semiconductor element having a layer including the organic semiconductor layer and the binder polymer.

The types of the binder polymer are not particularly limited, and well-known binder polymers can be used.

Examples of the binder polymer includes insulating polymers such as polystyrene, polycarbonate, polyarylate, polyester, polyamide, polyimide, polyurethane, polysiloxane, polysulfone, polymethyl methacrylate, polymethyl acrylate, cellulose, polyethylene, and polypropylene, and copolymers thereof, a semiconductor polymer such as polysilane, polycarbazole, polyarylamine, polyfluorene, polythiophene, polypyrrole, polyaniline, polyparaphenylenevinylene, polyacene, and polyheteroacene, and copolymers thereof, and rubber, and a thermoplastic elastomer.

Among these, as the binder polymer, a polymer compound (a polymer having a monomer unit having a benzene ring group) having a benzene ring is preferable. The content of the monomer unit having a benzene ring group is not particularly limited. However, the content is preferably 50 mol % or greater, more preferably 70 mol % or greater, and even more preferably 90 mol % or greater with respect to the entire monomer unit. The upper limit is not particularly limited, but examples of the upper limit include 100 mol %.

Examples of the binder polymer include polystyrene, poly(α-methylstyrene), polyvinyl cinnamate, poly(4-vinylphenyl), poly(4-methylstyrene), poly[bis(4-phenyl) (2,4,6-trimethylphenyl)amine], and poly[2,6-(4,4-bis(2-ethylhexyl)-4H cyclopenta[2,1-b;3,4-b']dithiophene)-alt-4,7-(2,1,3-benzothiadiazole)], and poly(α-methylstyrene) is particularly preferable.

A weight-average molecular weight of the binder polymer is not particularly limited, but is preferably 1,000 to 2,000,000, more preferably 3,000 to 1,000,000, and even more preferably 5,000 to 600,000.

In a case where a solvent described below is used, it is preferable that the binder polymer exhibits solubility higher than the solubility of the specific organic semiconductor compound in a used solvent. If the above aspect is adopted, mobility and heat stability of the obtained organic semiconductor are further improved.

A content of the binder polymer in the organic semiconductor layer of the organic semiconductor element of the present invention is preferably 1 to 200 parts by mass, more preferably 10 to 150 parts by mass, and even more preferably 20 to 120 parts by mass with respect to 100 parts by mass of the content of the specific organic semiconductor compound. If the content is within the above range, mobility and heat stability of the obtained organic semiconductor are further improved.

<Other Components>

Other components may be included other than the specific organic semiconductor compound and the binder polymer may be included in the organic semiconductor layer according to the organic semiconductor element of the present invention.

As other components, well-known additives and the like can be used.

In the organic semiconductor layer of the present invention, a content of the components other than the specific organic semiconductor compound and the binder polymer is preferably 10 mass % or less, more preferably 5 mass % or less, even more preferably 1 mass % or less, and particularly preferably 0.1 mass % or less with respect to the total mass of the organic semiconductor layer. If the content of other components is within the above range, film formability is improved, and mobility and heat stability of the obtained organic semiconductor are further improved.

The method of forming the organic semiconductor layer according to the organic semiconductor element of the present invention is not particularly limited. However, a desired organic semiconductor layer can be formed by applying the composition for forming the organic semiconductor film according to the present invention described below to a source electrode, a drain electrode, and a gate insulating film and performing a drying treatment, if necessary.

The organic semiconductor element of the present invention is preferably manufactured using the composition for forming an organic semiconductor film of the present invention described below.

A method of manufacturing an organic semiconductor film or an organic semiconductor element by using the composition for forming an organic semiconductor film of the present invention is not particularly limited, and known methods can be adopted. Examples thereof include a method (also referred to as "solution coating method") of manufacturing an organic semiconductor film by applying the composition onto a predetermined base material and if necessary, performing a drying treatment.

The method of applying the composition onto a base material is not particularly limited, and known methods can be adopted. Examples thereof include an ink jet printing method, a flexographic printing method, a bar coating method, a spin coating method, a knife coating method, a doctor blade method, and the like. Among these, an ink jet printing method, and a flexographic printing method are preferable.

Preferred examples of the flexographic printing method include an aspect in which a photosensitive resin plate is used as a flexographic printing plate. By printing the composition onto a substrate according to the aspect, a pattern can be easily formed.

Among the above methods, the method of manufacturing an organic semiconductor element of the present invention preferably includes a coating step of coating a substrate with the composition for forming an organic semiconductor film of the present invention and more preferably includes a coating step of causing the composition for forming an organic semiconductor film of the present invention to include a solvent, coating a substrate with the composition for forming an organic semiconductor film of the present invention, and a removing step of removing the solvent from the composition with which the substrate is coated.

The composition for forming the organic semiconductor film according to the present invention described below preferably includes a solvent and more preferably includes an organic solvent.

As the solvent, well-known solvents can be used.

Specifically, examples thereof include a hydrocarbon-based solvent such as hexane, octane, decane, toluene, xylene, mesitylene, ethylbenzene, decalin, and 1-methylnaphthalene, a ketone-based solvent such as acetone, methyl ethyl ketone, methyl isobutyl ketone, or cyclohexanone, a halogenated hydrocarbon-based solvent such as dichloromethane, chloroform, tetrachloromethane, dichloroethane, trichloroethane, tetrachloroethane, chlorobenzene, dichlorobenzene, and chlorotoluene, an ester-based solvent such as ethyl acetate, butyl acetate, and amyl acetate, an alcohol-based solvent such as methanol, propanol, butanol, pentanol, hexanol, cyclohexanol, methyl cellosolve, ethyl cellosolve, and ethylene glycol, an ether-based solvent such as dibutyl ether, tetrahydrofuran, dioxane, and anisole, an amide-based solvent such as N,N-dimethylformamide and N,N-dimethylacetamide, an imide-based solvent such as 1-methyl-2-pyrrolidone and 1-methyl-2-imidazolidinone, a sulfoxide-based solvent such as dimethylsulfoxide, and a nitrile-based solvent such as acetonitrile.

The solvent may be used singly or two or more types thereof may be used in combination.

Among these, a hydrocarbon-based solvent, a halogenated hydrocarbon-based solvent, an aromatic solvent, an aromatic heterocyclic solvent, and/or an ether-based solvent are preferable, and toluene, xylene, mesitylene, tetralin, dichlorobenzene and anisole are more preferable.

The boiling point of the solvent is preferably 100° C. or higher, in view of film formability. The boiling point of the solvent is more preferably 100° C. to 300° C., even more preferably 125° C. to 250° C., and particularly preferably 150° C. to 225° C.

It is preferable that a boiling point of the solvent of which the content is the greatest is 100° C. or higher and, it is more preferable that a boiling point of the entire solvent is 100° C. or higher.

In a case where the solvent is contained, the content of the specific organic semiconductor compound according to the composition for forming the organic semiconductor film of the present invention is preferably 0.05 to 50 mass %, more preferably 0.1 to 25 mass %, even more preferably 0.25 to 15 mass %, particularly preferably 0.4 to 10 mass % with respect to the total amount of the composition for forming the organic semiconductor film. The content of the binder polymer is preferably 0.01 to 50 mass %, more preferably 0.05 to 25 mass %, and even more preferably 0.1 to 10 mass % with respect to the total amount of the composition for forming the organic semiconductor film. If the content is in the range above, the coating properties are excellent, and the organic semiconductor film can be easily formed.

The drying treatment in the removing step is a treatment performed if necessary, and the optimal treatment conditions are suitably selected according to the type of the specific organic semiconductor compound used and the solvent. In view of further improving mobility and heat stability of the obtained organic semiconductor and improving productivity, a heating temperature is preferably 30° C. to 100° C. and more preferably 40° C. to 80° C., and a heating time is preferably 10 to 300 minutes and more preferably 30 to 180 minutes.

A film thickness of the formed organic semiconductor layer is not particularly limited. From the viewpoint of mobility and heat stability of the obtained organic semiconductor, the film thickness is preferably 10 to 500 nm and more preferably 30 to 200 nm.

The organic semiconductor element is not particularly limited, but is preferably an organic semiconductor element having 2 to 5 terminals, and more preferably an organic semiconductor element having 2 or 3 terminals.

It is preferable that the organic semiconductor element is not a photoelectric conversion element.

The organic semiconductor element according to the present invention is preferably a non-luminous organic semiconductor element.

Examples of a 2-terminal element include a rectifier diode, a constant voltage diode, a PIN diode, a Schottky barrier diode, a surge protection diode, a diac, a varistor, a tunnel diode, and the like.

Examples of a 3-terminal element include a bipolar transistor, a Darlington transistor, a field effect transistor, insulated gate bipolar transistor, a uni-junction transistor, a static induction transistor, a gate turn-off thyristor, a triac, a static induction thyristor, and the like.

Among these, a rectifier diode and transistors are preferable, and a field effect transistor is more preferable.

An aspect of the organic thin film transistor of the present invention will be described with reference to a drawing.

FIG. 1 is a schematic cross-sectional view of an aspect of an organic semiconductor element (organic thin film transistor (organic TFT)) of the present invention.

In FIG. 1, an organic thin film transistor 100 comprises a substrate 10, a gate electrode 20 disposed on the substrate 10, a gate insulating film 30 covering the gate electrode 20, a source electrode 40 and a drain electrode 42 which contact a surface of the gate insulating film 30 that is on the side opposite to the gate electrode 20 side, an organic semiconductor film 50 covering a surface of the gate insulating film 30 between the source electrode 40 and the drain electrode 42, and a sealing layer 60 covering each member. The organic thin film transistor 100 is a bottom gate-bottom contact type organic thin film transistor.

In FIG. 1, the organic semiconductor film 50 corresponds to a film formed of the composition described above.

Hereinafter, the substrate, the gate electrode, the gate insulating film, the source electrode, the drain electrode, the organic semiconductor film, the sealing layer, and methods for forming each of these will be specifically described.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of applicability to each device and costs, a glass substrate or a plastic substrate is preferable.

Examples of materials of the plastic substrate include a thermosetting resin (for example, an epoxy resin, a phenol resin, a polyimide resin, or a polyester resin (for example, polyethylene terephthalate (PET) or polyethylene naphthalate (PEN)) and a thermoplastic resin (for example, a phenoxy resin, a polyethersulfone, polysulfone, or polyphenylene sulfone).

Examples of materials of the ceramic substrate include alumina, aluminum nitride, zirconia, silicon, silicon nitride, silicon carbide, and the like.

Examples of materials of the glass substrate include soda lime glass, potash glass, borosilicate glass, quartz glass, aluminosilicate glass, lead glass, and the like.

<Gate Electrode, Source Electrode, and Drain Electrode>

Examples of materials of the gate electrode, the source electrode, and the drain electrode include a metal such as gold (Au), silver, aluminum (Al), copper, chromium, nickel, cobalt, titanium, platinum, tantalum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, a metal is preferable, and silver and aluminum are more preferable.

A thickness of each of the gate electrode, the source electrode, and the drain electrode is not particularly limited, but is preferably 20 to 200 nm.

A method of forming the gate electrode, the source electrode, and the drain electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. Furthermore, in a case where the electrode is patterned, examples of the patterning method include a photolithography method; a printing method such as ink jet printing, screen printing, offset printing, or relief printing; a mask vapor deposition method; and the like.

<Gate Insulating Film>

Examples of materials of the gate insulating film include a polymer such as polymethyl methacrylate, polystyrene, polyvinylphenol, polyimide, polycarbonate, polyester, polyvinylalcohol, polyvinyl acetate, polyurethane, polysulfone, polybenzoxazole, polysilsesquioxane, an epoxy resin, or a phenol resin; an oxide such as silicon dioxide, aluminum oxide, or titanium oxide; a nitride such as silicon nitride; and the like. Among these materials, in view of the compatibility with the organic semiconductor film, a polymer is preferable.

In a case where a polymer is used as the material of the gate insulating film, it is preferable to use a cross-linking agent (for example, melamine) in combination. If the cross-linking agent is used in combination, the polymer is cross-linked, and durability of the formed gate insulating film is improved.

A film thickness of the gate insulating film is not particularly limited, but is preferably 100 to 1,000 nm.

A method of forming the gate insulating film is not particularly limited, but examples thereof include a method of coating a substrate, on which the gate electrode is formed, with a composition for forming a gate insulating film, a method of vapor-depositing or sputtering the material of the gate insulating film onto a substrate on which the gate electrode is formed, and the like. A method of coating the aforementioned substrate with the composition for forming a gate insulating film is not particularly limited, and it is possible to use a known method (a bar coating method, a spin coating method, a knife coating method, or a doctor blade method).

In a case where the gate insulating film is formed by coating the substrate with the composition for forming a gate insulating film, for the purpose of removing the solvent, causing cross-linking, or the like, the composition may be heated (baked) after coating.

<Organic Semiconductor Film>

The organic semiconductor film according to the present invention is a film formed with the composition for forming the organic semiconductor film according to the present invention.

The method of forming an organic semiconductor film is not particularly limited, and it is possible to form a desired organic semiconductor film by applying the aforementioned composition to a source electrode, a drain electrode, and a gate insulating film and performing a dry treatment, if necessary.

<Binder Polymer Layer>

The organic semiconductor element of the present invention preferably has a layer of the aforementioned binder polymer between a layer containing the aforementioned organic semiconductor layer and an insulating film, and more preferably has a layer of the aforementioned binder polymer between the aforementioned organic semiconductor layer and the gate insulating film. A film thickness of the binder polymer layer is not particularly limited, but is preferably 20 to 500 nm. The binder polymer layer should be a layer containing the aforementioned polymer, and is preferably a layer composed of the aforementioned binder polymer.

A method of forming the binder polymer layer is not particularly limited, and a known method (a bar coating method, a spin coating method, a knife coating method, a doctor blade method, or an ink jet method) can be used.

In a case where the binder polymer layer is formed by performing coating by using a composition for forming a binder polymer layer, for the purpose of removing a solvent, causing cross-linking, or the like, the composition may be heated (baked) after coating.

<Sealing Layer>

From the viewpoint of durability, the organic semiconductor element of the present invention preferably comprises a sealing layer as an outermost layer. In the sealing layer, a known sealant can be used.

A thickness of the sealing layer is not particularly limited, but is preferably 0.2 to 10 μm.

A method of forming the sealing layer is not particularly limited, but examples thereof include a method of coating a substrate, on which the gate electrode, the gate insulating film, the source electrode, the drain electrode, and the organic semiconductor film are formed, with a composition for forming a sealing layer, and the like. Specific examples of the method of coating the substrate with the composition for forming a sealing layer are the same as the examples of the method of coating the substrate with the composition for forming a gate insulating film. In a case where the organic semiconductor film is formed by coating the substrate with the composition for forming a sealing layer, for the purpose of removing the solvent, causing cross-linking, or the like, the composition may be heated (baked) after coating.

Figure 2:
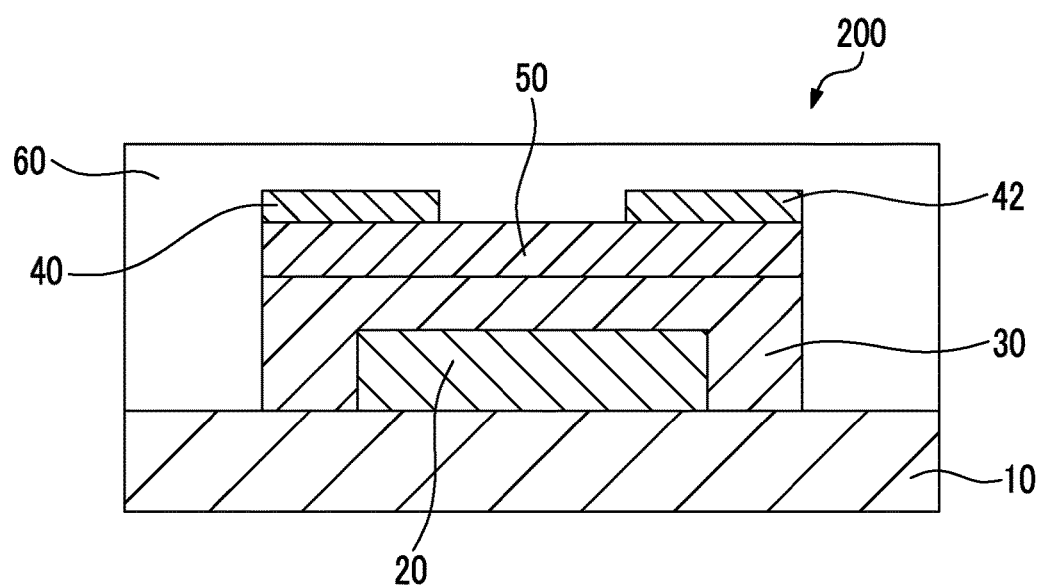
FIG. 2 is a schematic cross-sectional view of another aspect of the organic semiconductor element of the present invention.

FIG. 2 is a schematic cross-sectional view of another aspect of the organic semiconductor element (organic thin film transistor) of the present invention.

In FIG. 2, an organic thin film transistor 200 comprises the substrate 10, the gate electrode 20 disposed on the substrate 10, the gate insulating film 30 covering the gate electrode 20, the organic semiconductor film 50 disposed on the gate insulating film 30, the source electrode 40 and the drain electrode 42 disposed on the organic semiconductor film 50, and the sealing layer 60 covering each member. Herein, the source electrode 40 and the drain electrode 42 are formed using the aforementioned composition of the present invention. The organic thin film transistor 200 is a bottom gate-top contact type organic thin film transistor.

The substrate, the gate electrode, the gate insulating film, the source electrode, the drain electrode, the organic semiconductor film, and the sealing layer are as described above.

In FIGS. 1 and 2, the aspects of the bottom gate-bottom contact type organic thin film transistor and the bottom gate-top contact type organic thin film transistor were specifically described. However, the organic semiconductor element of the present invention can also suitably used in a top gate-bottom contact type organic thin film transistor and a top gate-top contact type organic thin film transistor.

The organic thin film transistor described above can be suitably used for electronic paper and a display device.

(Composition for Forming Organic Semiconductor Film)

The composition for forming the organic semiconductor film according to the present invention contains the specific organic semiconductor compound and a solvent.

The composition for forming the organic semiconductor film according to the present invention preferably contains a binder polymer.

The specific organic semiconductor compound, the binder polymer, and the solvent in the composition for forming the organic semiconductor film according to the present invention have the same meanings as the specific organic semiconductor compound, the binder polymer, and the solvent described above, and preferable aspects thereof are also the same.

The composition for forming the organic semiconductor film according to the present invention may include other component in addition to the specific organic semiconductor compound and the binder polymer.

As the component, well-known additives may be used.

The content of the component in addition to the specific organic semiconductor compound and the binder polymer in the composition for forming the organic semiconductor film according to the present invention is preferably 10 mass % or less, more preferably 5 mass % or less, even more preferably 1 mass % or less, and particularly preferably 0.1 mass % or less with respect to the total solid content of the composition for forming an organic semiconductor film. If the content is in the range described above, film formability is improved, and mobility and heat stability of the obtained organic semiconductor are further improved. The solid content is an amount of the components excluding the volatilizable component such as the solvent.

The viscosity of the composition for forming the organic semiconductor film according to the present invention is not particularly limited. However, in view of excellent coating properties, the viscosity is preferably 3 to 100 mPa·s, more preferably 5 to 50 mPa·s, and even more preferably 9 to 40 mPa·s. The viscosity according to the present invention refers to viscosity at 25° C.

As a method of measuring the viscosity, a measuring method in conformity of JIS Z8803 is preferable.

The method of manufacturing the composition for forming the organic semiconductor film according to the present invention is not particularly limited, and well-known methods can be applied. For example, a desired composition can be obtained by adding a specific amount of a specific organic semiconductor compound in the solvent and applying a suitable stirring treatment. In a case where the binder polymer is used, the specific organic semiconductor compound and the binder polymer are simultaneously or sequentially added, so as to suitably manufacture the composition.

(Organic Semiconductor Film)

The organic semiconductor film according to the present invention contains the specific organic semiconductor compound.

The organic semiconductor film according to the present invention preferably contains a binder polymer.

The specific organic semiconductor compound and the binder polymer in the organic semiconductor film according to the present invention have the same meanings as the specific organic semiconductor compound, a polymer and an oligomer that can be obtained by polymerizing the specific organic semiconductor compound, and the binder polymer described above in the organic semiconductor element according to the present invention, and preferable aspects thereof are also the same.

The composition for forming the organic semiconductor film according to the present invention may include other components in addition to the specific organic semiconductor compound, a polymer and an oligomer that can be obtained by polymerizing the specific organic semiconductor compound, and the binder polymer.

As the component, well-known additives may be used.

The content of the component in addition to the specific organic semiconductor compound, a polymer and an oligomer that can be obtained by polymerizing the specific organic semiconductor compound, and the binder polymer in the organic semiconductor film according to the present invention preferably 10 mass % or less, more preferably 5 mass % or less, even more preferably 1 mass % or less, and particularly preferably 0.1 mass % or less with respect to the total mass of the organic semiconductor film. If the content is in the range above, film formability is improved, and mobility and heat stability of the obtained organic semiconductor are further improved. The solid content is an amount of components other than the volatilizable components such as the solvent.

The film thickness of the organic semiconductor film according to the present invention is not particularly limited. However, in view of mobility and heat stability of the obtained organic semiconductor, the film thickness is preferably 10 to 500 nm and more preferably 30 to 200 nm.

The organic semiconductor film according to the present invention can be suitably used in the organic semiconductor element, and can be particularly suitably used in the organic transistor (organic thin film transistor).

The organic semiconductor film according to the present invention can be suitably manufactured by using the composition for forming the organic semiconductor film according to the present invention.

EXAMPLES

Hereinafter, the present invention will be more specifically described based on examples. The materials and the amount thereof used, the proportion of the materials, the content and procedure of treatments, and the like described in the following examples can be suitably changed within a scope that does not depart from the gist of the present invention. Accordingly, the scope of the present invention is not limited to the following specific examples. Herein, unless otherwise specified, "part" and "%" are based on mass.

(Organic Semiconductor Compound)

E-1 to E-8 which were organic semiconductor compounds used in the organic semiconductor layer were the same as E-1 to E-8 described as specific examples of the organic semiconductor compound.

Structures of Exemplary Compounds C-1 to C-3 were provided below.

C-1

M = 31000

C-2

Mw = 1200

C-3

Mn = 68000
Mw = 190000

<Synthesis of Compounds>

Compound E-1 was synthesized in a synthesis scheme below.

Specifically, with reference to Macromol., 2008, 41, 7287., Synthesis Intermediate IM was synthesized.

Synthesis Intermediate IM (92 mg, 0.2 mmol), 2,5-bis(trimethylstannyl)-3,6-didodecylthieno[3,2-b]thiophene (160 mg, 0.2 mmol), tri(o-tolyl) phosphine (4.9 mg, 0.016 mmol), tris(dibenzylideneacetone) dipalladium (3.7 mg, 0.004 mmol), and dehydrated chlorobenzene (20 mL) were mixed and were stirred at 130° C. for 72 hours under a nitrogen atmosphere. After the reaction solution was cooled to room temperature, 100 mL of methanol and 8 mL of concentrated hydrochloric acid were added and were stirred for 16 hours. The precipitated solid content was filtrated and washed with methanol, Soxhlet extraction was sequentially performed with ethanol, ethyl acetate, and chloroform, and soluble impurities were removed. Soxhlet extraction was performed with chlorobenzene, the solution was concentrated under reduced pressure, methanol was added, and the precipitated solid was filtered and washed with methanol, so as to obtain 70 mg of Compound E-1 (yield: 45%).

Compounds E-2 to E-8 were also synthesized in conformity with Compound E-1.

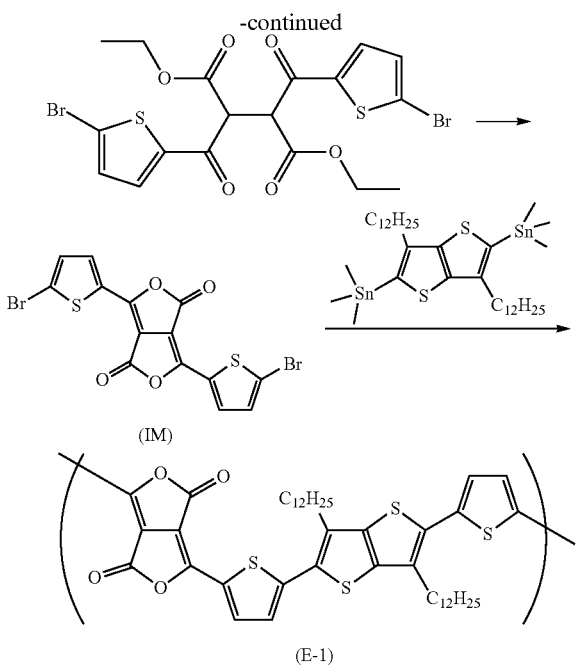

(IM)

(E-1)

Comparative Compounds C-1 and C-2 were compounds disclosed in Examples 2 and 12 of JP2007-516315A.

Comparative Compound C-3 was a compound disclosed in JP2014-507488A.

It was checked that in all of Compounds E-1 to E-8 and Exemplary Compounds C-1 to C-3, the purity (absorption intensity area ratio of 254 nm) was 99.8% or greater by high performance liquid chromatography (manufactured by Tosoh Corporation, TSKgel ODS-100Z).

<Reagent Used>

2-Acetyl-5-bromothiophene used in the synthesis of Compound E-1 was obtained from Tokyo Chemical Industry Co., Ltd.

2,5-Bis(trimethylstannyl)-3,6-didodecylthieno[3,2-b]thiophene was synthesized by the synthesis scheme below with reference to WO2005/111045A and J. Polym. Sci. Part A Polym. Chem., 2013, 51, 424. by using 3,6-dibromothieno[3,2-b]thiophene (manufactured by Tokyo Chemical Industry Co., Ltd.) and N-dodecyl zinc bromide (manufactured by Alfa Aesar) as starting materials.

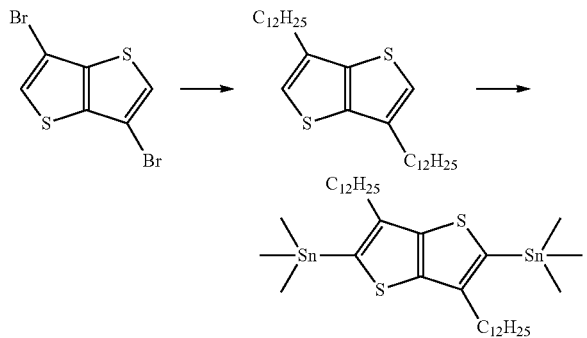

<Binder Polymer>

A polymer used as a binder polymer is provided below.

PαMS: Poly-α-methylstyrene, weight-average molecular weight: 437,000, manufactured by Sigma-Aldrich Co. LLC.

PTAA: Poly[bis(4-phenyl)(2,4,6-trimethylphenyl)amine], number-average molecular weight: 7,000 to 10,000, manufactured by Sigma-Aldrich Co. LLC.

PCPDTBT: Poly[2,6-(4,4-bis(2-ethylhexyl)-4H cyclopenta[2,1-b;3,4-b']dithiophene)-alt-4,7-(2,1,3-benzothiadiazole)], weight-average molecular weight: 7,000 to 20,000, manufactured by Sigma-Aldrich Co. LLC.

<Preparing Coating Liquid for Forming Organic Semiconductor Film>

An organic semiconductor compound (0.5 mass %)/a binder polymer (concentration disclosed in Table 1)/anisole (boiling point: 154° C.) presented in Table 1 was weighed in glass vial, stirring and mixing was performed for 10 minutes with a mix rotor (manufactured by As One Corporation), and filtration was performed with a 0.5 μm membrane filter, so as to obtain the coating liquid for forming the organic semiconductor film (the composition for forming the organic semiconductor film). In Table 1, "-" presented in a binder polymer indicates that the binder polymer was not included.

In Table 1, the concentration of the binder polymer disclosed in the brackets was mass % in the coating liquid.

<Manufacturing of TFT Element>

Al that became a gate electrode was vapor-deposited on the glass substrate (EAGLE XG: manufactured by Corning Incorporated) (Thickness: 50 nm). Spin coating was performed with a composition (solution (concentration of solid contents: 2 mass %) of propylene glycol monomethyl ether acetate (PGMEA) of polyvinylphenol/melamine=1 part by mass/1 part by mass (w/w)) for forming a gate insulating film, and the gate insulating film having a film thickness of 400 nm was formed by performing baking at 150° C. for 60 minutes. Shapes of source electrodes and drain electrodes (channel length: 40 μm, channel width: 200 μm) were drawn thereon, with silver ink (H-1, manufactured by Mitsubishi Materials Corporation) by using an inkjet device DMP-2831 (manufactured by Fujifilm Corporation). Thereafter, baking was performed in an oven at 180° C. for 30 minutes, sintering was performed, and source electrodes and drain electrodes were formed, so as to obtain an element substrate for TFT characteristic evaluation.

In a nitrogen glove box, spin coating was performed on the element substrate for TFT characteristic evaluation with the coating liquid for forming the respective organic semiconductor films (for 10 seconds at 500 rpm and for 30 seconds at 1,000 rpm), and drying was performed on a hot plate at 200° C. for 10 minutes, so as to form an organic semiconductor layer such that a bottom gate bottom contact-type organic TFT element was obtained.

<Characteristic Evaluation>

The following performance evaluation was carried out under the atmosphere by using a semiconductor characteristic evaluation device B2900A (manufactured by Agilent Technologies Japan, Ltd.).

(a) Carrier Mobility

Carrier mobility μ was calculated by applying a voltage of −60V between source electrodes-drain electrodes of the respective organic TFT elements, changing gate voltages in the range of +10 V to −60 V, and using an equation below indicating a drain current $I_d$.

$$I_d = (w/2L)\mu C_i(V_g - V_{th})^2$$

In the equation, L represents a gate length, w represents a gate width, $C_i$ represents capacity per unit area of an insulating layer, $V_g$ represents a gate voltage, and $V_{th}$ represents a threshold voltage.

As carrier mobility μ is higher, the carrier mobility μ is more preferable. In practice the carrier mobility μ is preferably $8.0 \times 10^{-3}$ cm$^2$/Vs or greater, more preferably $1.0 \times 10^{-2}$ cm$^2$/Vs or greater, and even more preferably $1.0 \times 10^{-1}$ cm$^2$/Vs or greater. If the mobility was lower than $1.0 \times 10^{-5}$ cm$^2$/Vs, characteristics were too small, it is presented that "<$1.0 \times 10^{-5}$" in the table, and thus the evaluation was not performed.

(b) Temporal Stability Under High Humidity

In a case where the respective manufactured organic thin film transistor elements were stored at 25° C., under the humidity of 80% RH for 24 hours and carrier mobility was measured, the carrier mobility maintenance ratio was evaluated in the following four stages and was set as an index of temporal stability under high humidity. As this value is greater, stability under high humidity is high. In practice, A or B was preferable, and A was more preferable.

Carrier mobility maintenance ratio after storage under high humidity (%)=mobility (after storage under high humidity)/mobility (before storage under high humidity)

A: 80% or greater
B: 60% or greater and less than 80%
C: 40% or greater and less than 60%
D: Less than 40%

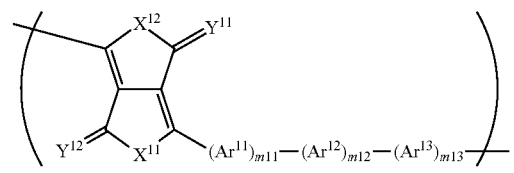

(1)

in Formula 1, $X^{11}$ and $X^{12}$ each independently represent any one of $CH_2$, $CR^{11}{}_2$, O, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of

TABLE 1

| | Element Number | Organic semiconductor | Mn | Mw | Binder polymer (mass %) | Carrier mobility (cm²/Vs) | Temporal stability under high humidity |
|---|---|---|---|---|---|---|---|
| Example 1 | Element 1-1 | Compound E-1 | 100,000 | 440,000 | — | $7.3 \times 10^{-2}$ | A |
| Example 2 | Element 1-2 | Compound E-1 | 100,000 | 440,000 | PαMS (0.5) | $7.8 \times 10^{-2}$ | A |
| Example 3 | Element 1-3 | Compound E-2 | 25,000 | 97,000 | — | $8.5 \times 10^{-2}$ | A |
| Example 4 | Element 1-4 | Compound E-3 | 45,000 | 160,000 | — | $9.1 \times 10^{-2}$ | A |
| Example 5 | Element 1-5 | Compound E-4 | 82,000 | 280,000 | — | $2.3 \times 10^{-1}$ | A |
| Example 6 | Element 1-6 | Compound E-4 | 82,000 | 280,000 | PTAA (0.125) | $2.4 \times 10^{-1}$ | A |
| Example 7 | Element 1-7 | Compound E-5 | 65,000 | 250,000 | — | $8.8 \times 10^{-2}$ | A |
| Example 8 | Element 1-8 | Compound E-5 | 65,000 | 250,000 | PCPDTBT (0.25) | $9.1 \times 10^{-2}$ | A |
| Example 9 | Element 1-9 | Compound E-6 | 87,000 | 320,000 | — | $2.5 \times 10^{-2}$ | B |
| Example 10 | Element 1-10 | Compound E-7 | 70,000 | 310,000 | — | $1.1 \times 10^{-2}$ | A |
| Example 11 | Element 1-11 | Compound E-8 | 15,000 | 57,000 | — | $9.3 \times 10^{-3}$ | A |
| Comparative Example 1 | Element 1-12 | Comparative Compound 1 | 10,000 | 31,000 | — | $1.5 \times 10^{-5}$ | D |
| Comparative Example 2 | Element 1-13 | Comparative Compound 2 | 400 | 1,250 | — | $<1.0 \times 10^{-5}$ | — |
| Comparative Example 3 | Element 1-14 | Comparative Compound 3 | 68,000 | 190,000 | — | $4.1 \times 10^{-3}$ | D |

EXPLANATION OF REFERENCES

10: substrate
20: gate electrode
30: gate insulating film
40: source electrode
42: drain electrode
50: organic semiconductor film
60: sealing layer
100, 200: organic thin film transistor

What is claimed is:

1. An organic semiconductor element comprising:
an organic semiconductor layer containing an organic semiconductor having a repeating unit represented by Formula 1, $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, m13 represents an integer of 0 to 2, and a sum of m11, m12, and m13 is 1 or greater.

2. The organic semiconductor element according to claim 1,
wherein both of $X^{11}$ and $X^{12}$ are O.

3. The organic semiconductor element according to claim 1,
wherein both of $Y^{11}$ and $Y^{12}$ are O or S.

4. The organic semiconductor element according to claim 1,
wherein the repeating unit represented by Formula 1 is a repeating unit represented by Formula 2,

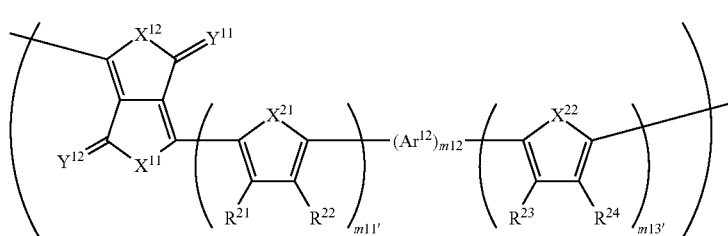

(2)

in Formula 2, $X^{11}$ and $X^{12}$ each independently represent any one of $CH_2$, $CR^{11}{}_2$, O, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}{}_2$, O, S, Se, and $SiR^{11'}{}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, m13' represents an integer of 0 to 2, and a sum of m11', m12', and m13' is 1 or greater.

5. A compound comprising:
a repeating unit represented by Formula 1,

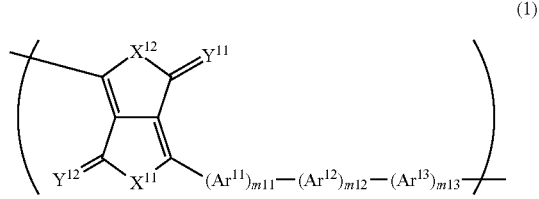

(1)

in Formula 1, $X^{11}$ and $X^{12}$ each independently represent any one of $CH_2$, $CR^{11}{}_2$, O, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, m13 represents an integer of 0 to 2, and a sum of m11, m12, and m13 is 1 or greater.

6. The compound according to claim 5,
wherein both of $X^{11}$ and $X^{12}$ are O.
7. The compound according to claim 5,
wherein both of $Y^{11}$ and $Y^{12}$ are O or S.
8. The compound according to claim 5,
wherein the repeating unit represented by Formula 1 is a repeating unit represented by Formula 2,

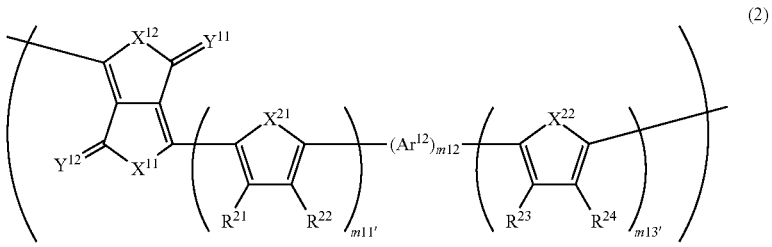

(2)

in Formula 2, $X^{11}$ and $X^{12}$ each independently represent any one of $CH_2$, $CR^{11}{}_2$, O, Se, and $SiR^{11}{}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}{}_2$, O, S, Se, and $SiR^{11'}{}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, m13' represents an integer of 0 to 2, and a sum of m11', m12', and m13' is 1 or greater.

9. The compound according to claim 5, which is an organic semiconductor.

10. A composition for forming an organic semiconductor film, comprising:
a compound having a repeating unit represented by Formula 1; and
a solvent,

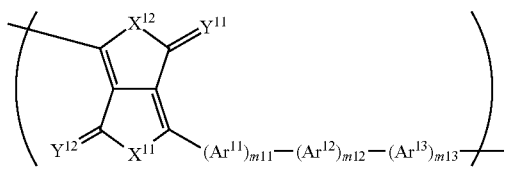

in Formula 1, $X^{11}$ and $X^{12}$ each independently represent any one of $CH_2$, $CR^{11}_2$, O, Se, and $SiR^{11}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, m13 represents an integer of 0 to 2, and a sum of m11, m12, and m13 is 1 or greater.

11. The composition for forming an organic semiconductor film according to claim 10,
wherein both of $X^{11}$ and $X^{12}$ are O.

12. The composition for forming an organic semiconductor film according to claim 10,
wherein both of $Y^{11}$ and $Y^{12}$ are O or S.

13. The composition for forming an organic semiconductor film according to claim 10,
wherein the repeating unit represented by Formula 1 is a repeating unit represented by Formula 2,

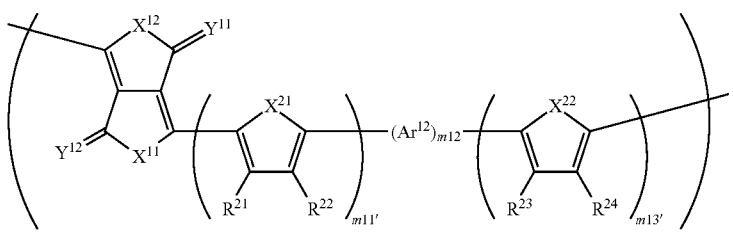

in Formula 2, $X^{11}$ and $X^{12}$ each independently represent any one of $CH_2$, $CR^{11}_2$, O, Se, and $SiR^{11}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}_2$, O, S, Se, and $SiR^{11'}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, m13' represents an integer of 0 to 2, and a sum of m11', m12', and m13' is 1 or greater.

14. The composition for forming an organic semiconductor film according to claim 10, further comprising:
a binder polymer.

15. A method of manufacturing an organic semiconductor element, comprising:
a coating step of coating a substrate with the composition for forming an organic semiconductor film according to claim 10.

16. An organic semiconductor film comprising:
a compound having a repeating unit represented by Formula 1,

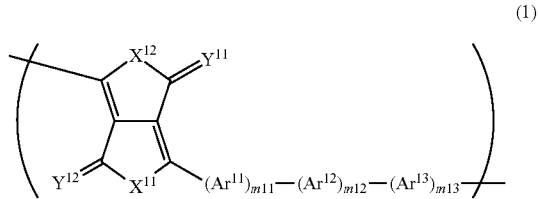

in Formula 1, $X^{11}$ and $X^{12}$ each independently represent any one of $CH_2$, $CR^{11}_2$, O, Se, and $SiR^{11}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{11}$, $Ar^{12}$, and $Ar^{13}$ each independently represent an aromatic hydrocarbon group, an aromatic heterocyclic group, a vinylene group, or an ethynylene group, m11 represents an integer of 0 to 2, m12 represents an integer of 0 to 4, m13 represents an integer of 0 to 2, and a sum of m11, m12, and m13 is 1 or greater.

17. The organic semiconductor film according to claim 16,
wherein both of $X^{11}$ and $X^{12}$ are O.

18. The organic semiconductor film according to claim 16,
wherein both of $Y^{11}$ and $Y^{12}$ are O or S.

19. The organic semiconductor film according to claim 16,
wherein the repeating unit represented by Formula 1 is a repeating unit represented by Formula 2,

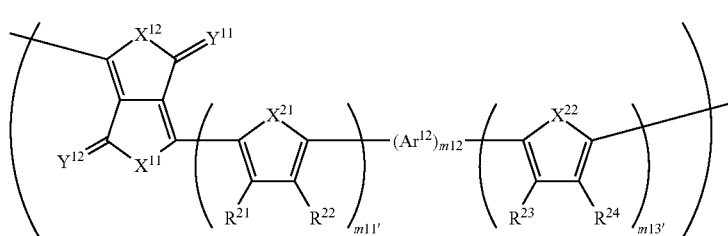

(2)

in Formula 2, $X^{11}$ and $X^{12}$ each independently represent any one of $CH_2$, $CR^{11}_2$, O, Se, and $SiR^{11}_2$, $R^{11}$'s each independently represent a monovalent organic group, $Y^{11}$ and $Y^{12}$ each independently represent O, S, N—CN, or $CQ_2$, Q represents CN, $CF_3$, $C(=O)R^{12}$, $C(=O)OR^{12}$, or $SO_2R^{12}$, $R^{12}$'s each independently represent a monovalent organic group, a plurality of $R^{12}$'s may be bonded to each other to form a ring, $Ar^{12}$ represents an aromatic hydrocarbon group, an aromatic heterocyclic group, a vinylene group, or an ethynylene group, m12 represents an integer of 0 to 4, $X^{21}$ and $X^{22}$ each independently represent any one of $CH_2$, $CR^{11'}_2$, O, S, Se, and $SiR^{11'}_2$, $R^{11'}$'s each independently represent a hydrogen atom or a monovalent organic group, $R^{21}$ to $R^{24}$ each independently represent a hydrogen atom or a monovalent organic group, m11' represents an integer of 0 to 2, m13' represents an integer of 0 to 2, and a sum of m11', m12', and m13' is 1 or greater.

20. The organic semiconductor film according to claim 16, which is manufactured by a solution coating method.

\* \* \* \* \*